United States Patent [19] [11] Patent Number: 6,043,042
Shone et al. [45] Date of Patent: Mar. 28, 2000

[54] ANTIBODY FOR A TOXIN ASSAY, AND METHOD OF OBTAINING SAME

[75] Inventors: Clifford Charles Shone, Salisbury; Bassam Hallis, Wiltshire; Benjamin Arthur Frederick James, Wiltshire; Conrad Padraig Quinn, Wiltshire, all of United Kingdom

[73] Assignee: Microbiobiological Research Authority, Salisbury, United Kingdom

[21] Appl. No.: 09/015,960

[22] Filed: Jan. 30, 1998

Related U.S. Application Data

[60] Division of application No. 08/760,001, Dec. 3, 1996, Pat. No. 5,962,637, which is a continuation-in-part of application No. PCT/GB95/01279, Jun. 2, 1995.

[30] Foreign Application Priority Data

Jun. 3, 1994 [GB] United Kingdom .................... 9411138

[51] Int. Cl.[7] ........................ G01N 33/53; G01N 33/573; G07K 16/00; C12Q 1/04; C12Q 1/06

[52] U.S. Cl. .......................... 435/7.1; 530/389.5; 435/7.4; 435/34; 435/39

[58] Field of Search .......................... 530/389.5; 435/7.1, 435/7.4, 34, 39

[56] References Cited

U.S. PATENT DOCUMENTS 5,171,662  12/1992  Sharma ....................................... 435/5

FOREIGN PATENT DOCUMENTS 0 529 719 A1  3/1993  European Pat. Off. ................. 275/24

OTHER PUBLICATIONS

Schiavo, et al., Tetanus and botulinum–B neurotoxins block neutransmitter release by proteolytic cleavage of synaptobrevin, Nature, vol. 359, pp. 832–835, see entire article. Oct. 1992.

Sollner, et al., Snap receptors implicated in vesicle targeting and fusion, Nature, vol. 362, pp. 318–324, Mar. 1993.

Doellgast, et al., Sensitive Enzyme–Linked Immunosorbent Assay for Detection of Clostridium botulinum Neurotoxins A, B, and E Using Signal Amplification via Enzyme–Linked Coagulation Assay, J. Clin. Microbiol., vol. 31, No. 9, pp. 2402–2409, see page 2402, Sep. 1993.

Foran, P. et al., "Differences in the Protease Activities of Tetanus and Botulinum B Toxins Revealed by the Cleavage of Vesicle–Associated Membrane Protein and Various Sized Fragments," *Biochem.* 33:15365–15374 (Dec. 27, 1994).

Rossetto, O. et al., "Snare Motif and Neurotoxins," *Nature* 372:415–416 (Dec. 1, 1994).

Shone, C. and Roberts, A., "Peptide Substrate Specificity and Properties of the Zinc–Endopeptides Activity of Botulinum Type B Neurotoxin," *Eur. J. Biochem.* 225:263–270 (Oct. 1, 1994).

Oyler, G.A. et al., "The Identification of a Novel Synaptosomal–associated Protein, Snap–25, Differentially Expressed by Neuronal Subpopulations," *J. Cell. Bio.* 109:3039–3052 (1989).

*Primary Examiner*—Hankyel Park
*Attorney, Agent, or Firm*—Sterne, Kessler, Goldstein & Fox P.L.L.C.

[57] ABSTRACT

A toxin assay that uses a substrate for cleavage by the toxin and antibodies that do not recognize the substrate but recognize and bind to the product of cleavage of the substrate by the toxin. The substrate can be a nerve cell peptide when the assay is for botulinum toxin or tetanus toxin.

13 Claims, 7 Drawing Sheets

FIG. 1 ASSAY FOR BOTULINUM TOXIN

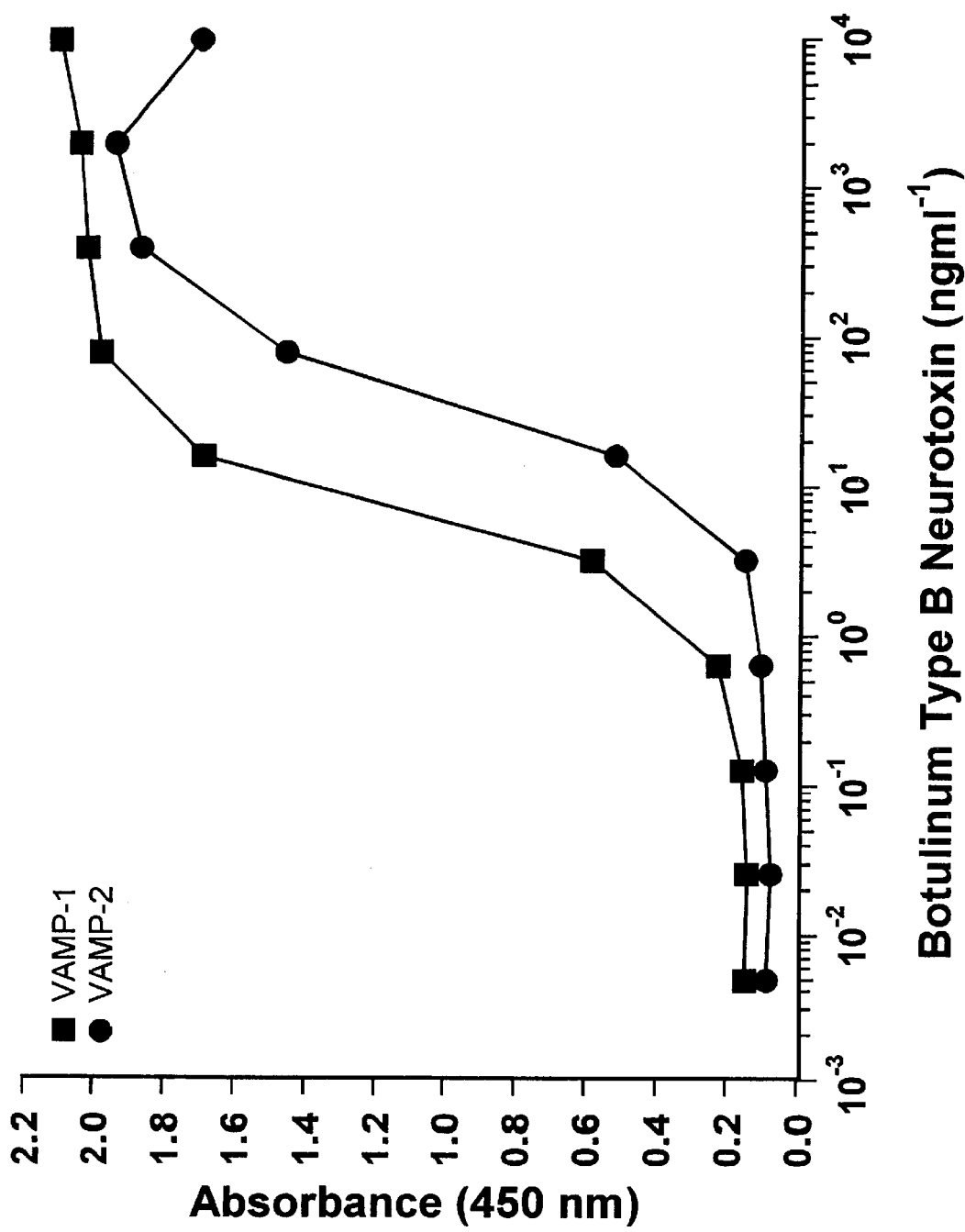

FIG. 3 Specificity of cleavage assay for BoNT/B

■ BoNT/B
● BoNT/F
◀ Tetanus
▼ BoNT/B + EDTA

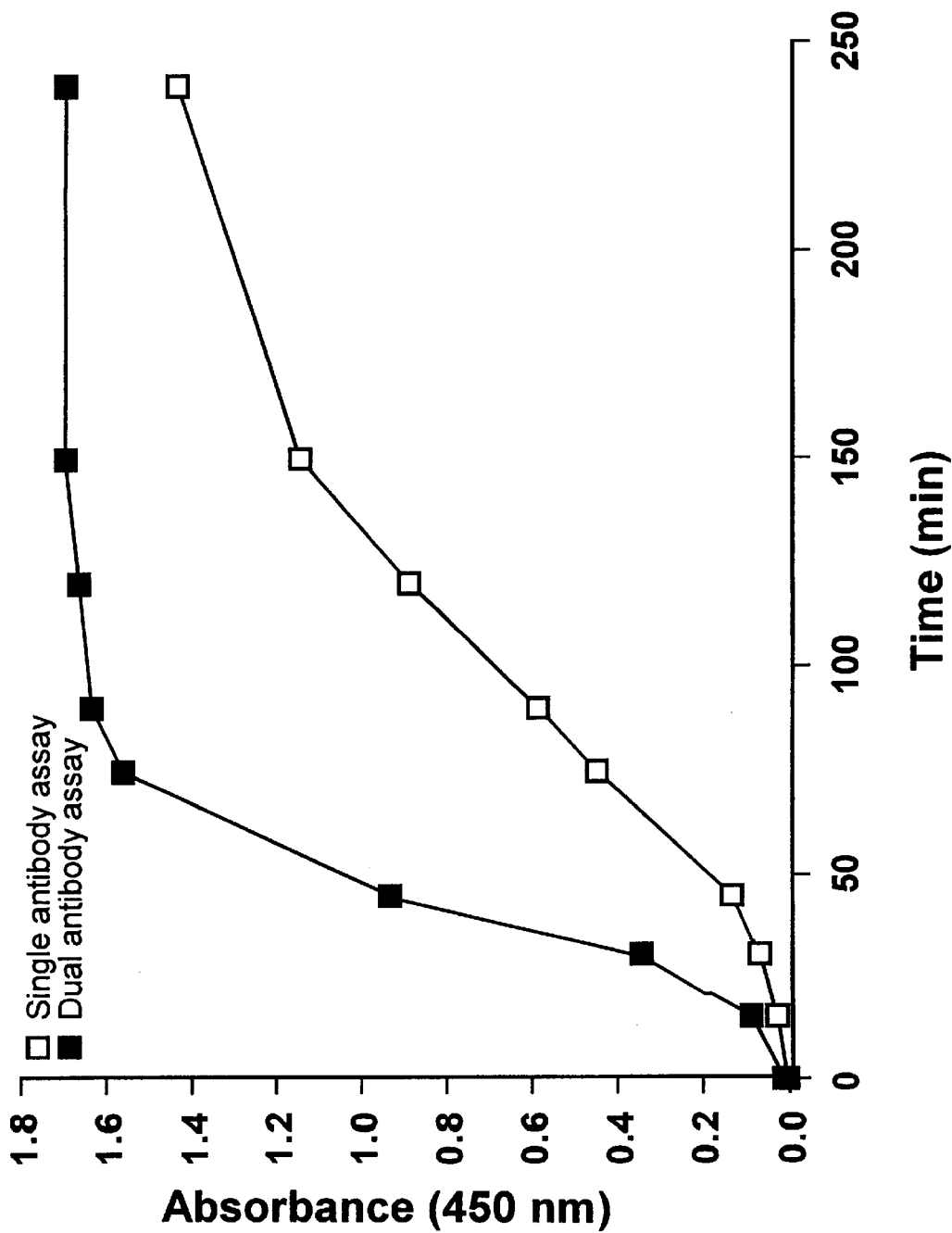
FIG. 4 Kinetics of the cleavage assay for BoNT/A using both single and dual antibody assay procedures.

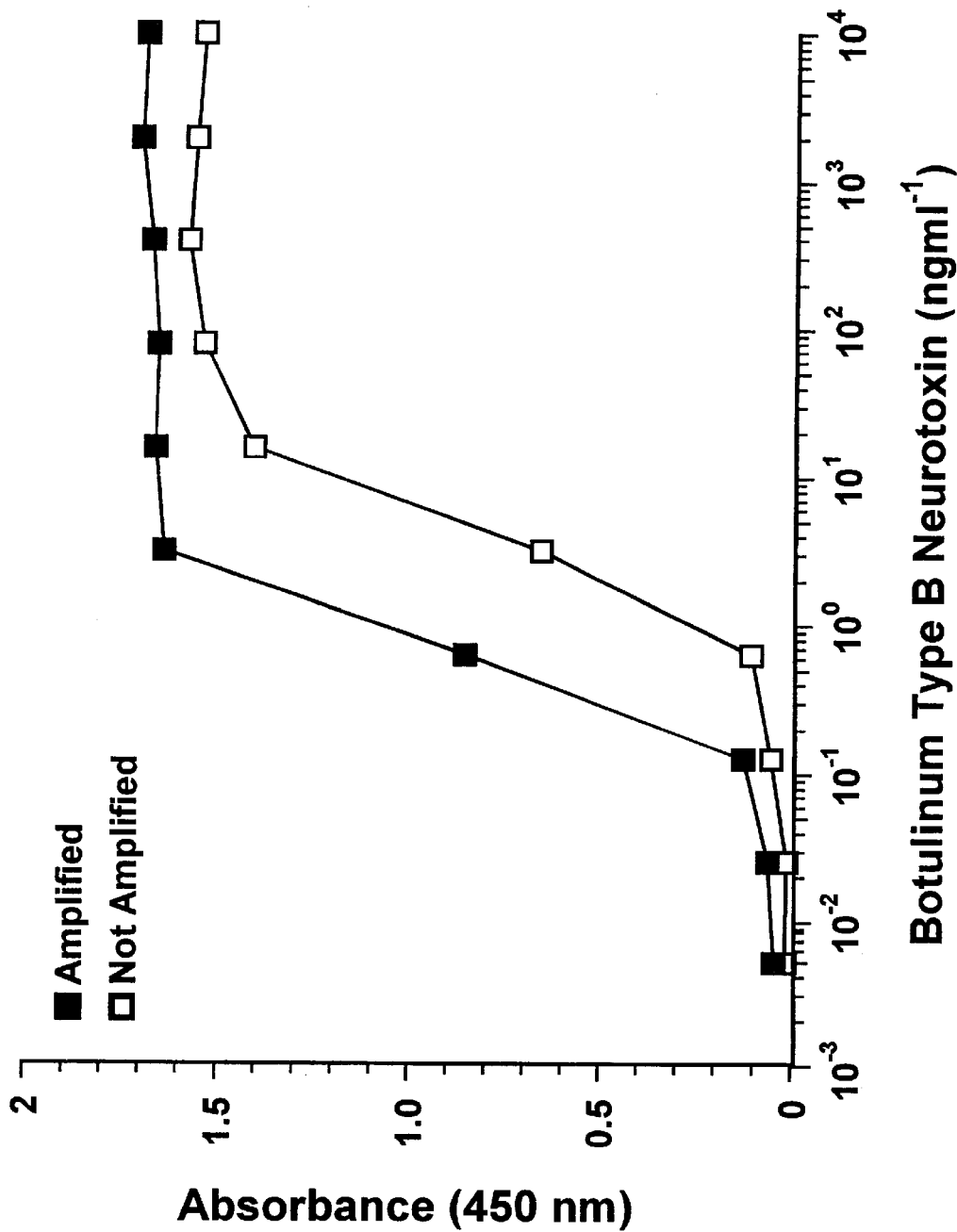
FIG. 5 The amplification of the BoNT/B assay using the ELAST™ system

FIG. 6 Effect of limited trypsin-treatment of BoNT/B on the sensitivity of the cleavage assay for the neurotoxin □ BoNT/B
■ BoNT/B + Trypsin
○ BoNT/B (Ampl.)
● BoNT/B + Trypsin (Ampl.)

Absorbance (450 nm)
Botulinum type B neurotoxin (ngml$^{-1}$)

FIG. 7 Cleavage assay for BoNT/A

ANTIBODY FOR A TOXIN ASSAY, AND METHOD OF OBTAINING SAME

CROSS REFERENCE TO RELATED APPLICATION

This is a divisional of application Ser. No. 08/760,001, filed Dec. 3, 1996, now U.S. Pat. No. 5,962,637 which is a continuation-in-part of PCT/GB95/01279, filed Jun. 2, 1995, the contents of which are fully incorporated by reference herein.

BACKGROUND OF THE INVENTION

1. Field of the Invention

The invention is in the field of antibody-based assays for toxins having peptidase activity. In particular, this invention relates to assays for toxins, in particular botulinum neurotoxins and tetanus toxins. The invention also relates to antibodies useful in the assays and to peptides immobilized on solid phase supports that are useful in the assays.

2. Related Art

The botulinum neurotoxins are a family of structurally similar, but antigenically different protein neurotoxins which act on the peripheral nervous system to block neuromuscular transmission. These neurotoxins are extremely potent, with a human lethal dose in the order of micrograms, and give rise to the rare but frequently fatal disease, botulism. Assays for the botulinum neurotoxins are currently used in both the food and pharmaceutical industry. The food industry employs assays for the botulinum neurotoxins to validate new food packaging methods and to ensure food safety. With the growing clinical use of the botulinum toxins, the pharmaceutical industry requires accurate assays for these toxins for both product formulation and quality control.

It is known to assay for botulinum toxin in foodstuffs using the mouse lethality test. This test has been the industry standard for many years, though over the past 10 years a number of immunoassay methods have been developed in an attempt to replace the mouse test in the majority of applications.

One such assay operates by addition of a test sample to a plate or column to which is attached an antibody that binds to toxin present in the sample. A further antibody is typically used to detect bound toxin. These enzyme-linked immunoassays (ELISA) have the advantages that they are specific to one botulinum toxin type and can be performed rapidly, in less than 2 hours. The ELISAs, however, suffer from several drawbacks:

(a) They do not measure the biological activity of the toxins, (b) They cannot distinguish between active and inactive toxin, and (c) Due to antigenic variations some toxins are not detected by these assays which therefore give rise to false negatives.

The botulinum neurotoxins have recently been shown to possess highly specific zinc-endopeptidase activities within their light sub-units. Depending on the neurotoxin type these act to cleave small proteins within the nerve cell which are involved in neurotransmitter release. Botulinum types A and E toxins cleave protein SNAP-25. Botulinum types B, D, F and G and tetanus toxins cleave vesicle-associated membrane protein (VAMP-also called synaptobrevin). Botulinum type C toxin cleaves the protein syntaxin.

In the development of further toxin assays, various procedures have been devised for the evaluation of endopeptidase activities. Liquid chromatography procedures are known and are based on resolution of the peptide product and subsequent evaluation. These procedures are time-consuming, expensive and do not lend themselves readily to automation. It is also known to use spectrophotometric methods, requiring the development of suitable chromogenic peptide reagents. Such methods provide a continuous precise assay for endopeptidases. Spectrophotometric methods, however, require relatively pure preparations of enzyme and are not normally suitable for evaluation of endopeptidase activities in crude or particulate samples.

Despite these efforts, at present, the only convenient assay for the biological activity of the botulinum neurotoxins, and the only assay that is FDA approved, remains the mouse lethality test. This test suffers from a number of drawbacks:

(a) It is expensive and uses large numbers of laboratory animals, (b) It is non-specific unless performed in parallel with toxin neutralization tests using specific anti-sera, and (c) It is not very accurate unless large animal groups are used.

The present invention describes a novel assay system for toxins, using novel reagents. The assay aims to overcome or at least mitigate many of the drawbacks of present in vitro assays for these toxins.

SUMMARY OF THE INVENTION

The invention relates to an assay for botulinum toxin or tetanus toxin comprising the steps of:

(a) combining a test compound with a substrate and with antibody, wherein the substrate has a cleavage site for the toxin and when cleaved by toxin forms a product, and wherein the antibody binds to the product but not to the substrate; and (b) testing for the presence of antibody bound to the product, which product is attached to a solid phase assay component.

Preferably, in the practice of this invention, the substrate is a peptide or a protein which is cleaved by the toxin to generate new peptides having N- and C-terminal ends. In addition, the peptide substrate is attached to a solid phase component of the assay.

The assay according to the invention may utilize assay components (a) and (b):

(a) a peptide linked to a solid-phase, the peptide being cleavable by the toxin to generate a cleavage product, (b) an antibody that binds to the cleavage product but not to the peptide, and the assay may comprise the steps of:

(i) combining a test compound that may contain or consist of the toxin with the solid-phase peptide to form an assay mixture, (ii) subsequently or simultaneously combining the assay mixture with the antibody, and (iii) subsequently or simultaneously determining whether there has been formed any conjugate between the antibody and the cleavage product.

Preferably, the step (i) of the assay is carried out in the presence of a zinc compound. In addition, the peptide is selected from intact peptides or fragments thereof selected from the group consisting of VAMP; a VAMP analog; a VAMP isoform; SNAP-25; a SNAP-25 analog; a SNAP-25 isoform; syntaxin; a syntaxin analog; and a syntaxin isoform; or a fragment thereof In this embodiment, the assay comprises:

(i) combining the test compound with a solid phase comprising a peptide selected from the group consisting of VAMP; a VAMP analog; a VAMP isoform; SNAP-25; a SNAP-25 analog; a SNAP-25 isoform; syntaxin; a syntaxin analog; and a syntaxin isoform; or a fragment thereof, (ii) washing the test compound from the solid phase, (iii) combining the solid phase with an antibody adapted for binding selectively with peptide cleaved by toxin, and (iv) detecting a conjugate of the antibody with cleaved peptide.

In another embodiment, the assay comprises:

(i) adding a test solution to an assay plate comprising immobilized peptide, the peptide being selected from the group consisting of VAMP; a VAMP analog; a VAMP isoform; SNAP-25; a SNAP-25 analog; a SNAP-25 isoform; syntaxin; a syntaxin analog; and a syntaxin isoform; or a fragment thereof, (ii) incubating the assay plate, (iii) washing the plate with a buffer, (iv) adding to the plate an antibody solution, said solution comprising an antibody adapted selectively to bind to a peptide selected from the group consisting of(l) a peptide the C-terminal end of which is selected from the group consisting of SEQ ID NOS: 1, 3 and 5, and (2) a peptide the N-terminal end of which is selected from the group consisting of SEQ ID NOS: 2, 4 and 6, (v) incubating the assay plate, (vi) washing the plate with a buffer, and (vii) measuring the presence of antibody on the assay plate.

In this embodiment, the antibody may be linked to an enzyme and the presence of antibody on the plate is measured by adding an enzyme substrate and measuring the conversion of the substrate into detectable product. The detectable product may be colored and measured by absorbance at a selected wavelength.

In the practice of the invention, the inactive toxin present in the test compound may be converted to active toxin. This may be accomplished by adding a protease to the test compound.

The antibody-peptide conjugate may be detected using a further antibody specific to the first antibody and linked to an enzyme.

The present invention also relates to a method of obtaining an antibody, the antibody being for use in an assay for botulinum toxin or tetanus toxin, the method comprising identifying a macromolecule that is cleaved by the toxin into cleavage products, immunizing an animal against one of the cleavage products, isolating antibodies that bind to said one of the cleavage products and recovering antibody that does not cross-react with the macromolecule. In this embodiment, the method comprises:

(i) identifying a macromolecule that is cleaved by the toxin, thereby forming at least first and second cleavage products, (ii) immunizing an animal with a selected one of the cleavage products, (iii) isolating from the animal an antibody that binds to the selected cleavage product, and (iv) checking the antibody does not bind to the macromolecule.

Preferably, the method comprises:

(i) immunizing an animal with an antigen selected from the group consisting of (1) SEQ ID NO.s 1–6; and (2) a carrier molecule linked to (1), and (ii) isolating from the animal an antibody that binds to the antigen.

In the practice of this aspect of the invention, the antigen may be linked to a carrier protein, e.g. selected from Keyhole Limpet Hemocyanin, Bovine Serum Albumin and Ovalbumin.

The invention also relates to an antibody for use in the assay according to the invention, characterized in that it does not bind to a peptide selected from the group consisting of VAMP; a VAMP analog; a VAMP isoform; SNAP-25; a SNAP-25 analog; a SNAP-25 isoform; syntaxin; a syntaxin analog; and a syntaxin isoform; or a fragment thereof; but does bind to a product of cleavage by the toxin of one of these peptides. Preferably, the antibody is adapted to bind to an antigen of formula:

P-Q-X wherein X is a peptide selected from the group consisting of SEQ ID NOS: 1–7 and is covalently linked at one end to P-Q, and wherein P-Q is a carrier in which P is a carrier protein and Q is an amino acid or an amino acid sequence adapted to attach peptide X to carrier P.

The invention also relates to a component for a toxin assay comprising a peptide selected from the group consisting of VAMP; a VAMP analog; a VAMP isoform; SNAP-25; a SNAP-25 analog; a SNAP-25 isoform; syntaxin; a syntaxin analog; and a syntaxin isoform; or a fragment thereof; and wherein the peptide is immobilized on a solid phase.

The invention also relates to a toxin assay kit comprising (1) an assay component according to the invention;

(2) (a) an antibody according to the invention which is linked to or including an enzyme, or (b) an antibody according to the invention which is unlabeled with an enzyme and a second antibody adapted to bind to the first antibody and linked to or including an enzyme, and (3) a substrate for the enzyme.

BRIEF DESCRIPTION OF THE FIGURES

Figure 1:
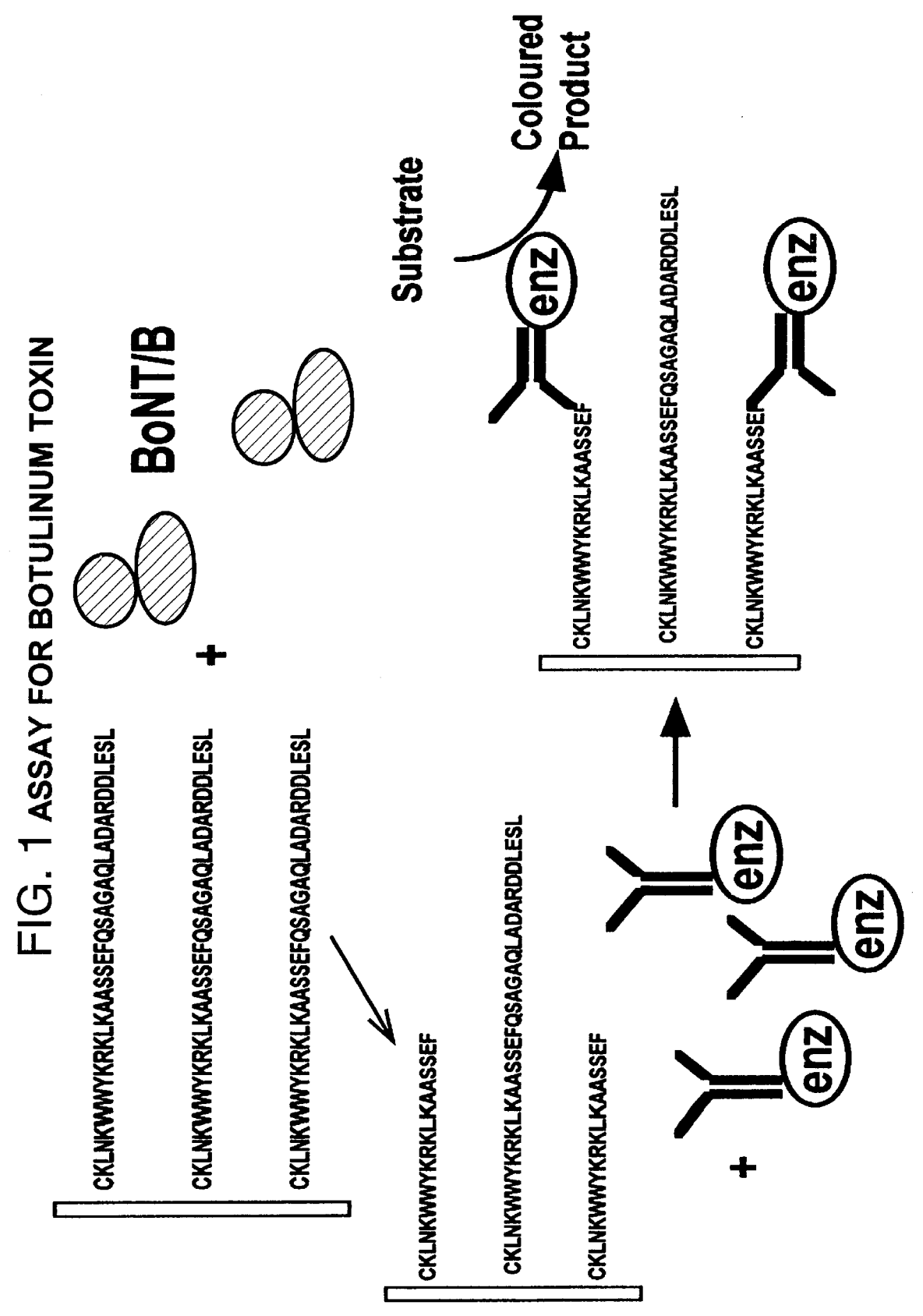

FIG. 1 depicts a schematic representation of a botulinum toxin assay.

FIG. 2 depicts a graph with the results of a cleavage assay for botulinum toxin according to Example 1.

FIG. 3 depicts a graph showing the specificity of the cleavage assay for botulinum toxin according to Example 1.

FIG. 4 depicts a graph showing the kinetics of the cleavage assay for botulinum toxin, using both the single and dual antibody assay according to Example 1.

FIG. 5 depicts a graph with the results of the botulinum toxin assay of Example 1 which is further improved and made more sensitive by signal amplification and toxin activation procedures described in Example 2.

FIG. 6 depicts a graph showing the effect of limited trypsin-treatment of BoNT0B on the sensitivity of the cleavage assay according to the procedures described in Example 2.

FIG. 7 depicts a graph showing the results achieved using the botulinum toxin assay of Example 4.

DETAILED DESCRIPTION OF THE PREFERRED EMBODIMENTS

Accordingly, a first aspect of the invention provides a toxin assay comprising the steps:

(a) combining a test compound with (i) a substrate that has a cleavage site for the toxin and (ii) antibodies that bind to the cleaved substrate but not to uncleaved substrate, and (b) testing for the presence of antibodies bound to the cleaved substrate.

This has the advantage that the assay is capable of distinguishing between active and inactive toxin—as inactive toxin will have reduced or no activity. Also, antigenic variation between toxins of the same group will not significantly affect the working of the assay, because it is toxin activity (ability to cleave the substrate) that is being measured and not the precise antigenic make-up of the toxin.

In use of an embodiment of the invention, cleavage of the substrate by toxin present in the test compound generates a product that is recognized by and binds to the antibodies of the assay, which antibodies do not bind to the uncleaved substrate. It is preferred that the toxin cleaves the substrate at a single location so as to generate two products, one of which binds to the antibodies.

In another embodiment of the invention, the substrate is a peptide or protein that contains a cleavage site for the toxin and cleavage of the substrate generates new peptides having N- and C-terminal ends. The antibody binds to one of these newly formed peptides. A particular assay of the invention is for assay of a botulinum toxin or tetanus toxin and the assay determines whether amounts of one of these toxins are present in the test compound. In this particular assay, the substrate of the invention is a peptide or a protein that is cleaved by endopeptidase activity of the botulinum toxin or tetanus toxin. An advantage of the assay is that it distinguishes between active and inactive toxin, as the assay is a measurement of the peptidase activity present in the sample.

Suitable substrates for the toxin assay include the protein families VAMP (also known as synaptobrevin), SNAP-25 and syntaxin. Each of these protein families comprises several isoforms and analogues which are detailed below.

In mammals, VAMP (or synaptobrevin) has number of isoforms and analogues. These are VAMP/synaptobrevin isoforms 1 and 2, and cellubrevin which is found in non-secretary cells. There may be other isoforms in exocrine cells. In yeasts, there are structurally related proteins known as BOS1, SEC22, BET1, SNC1 and SNC2, see the review "From yeast to man" by FerroNovick and Jahn in *Nature* 370, Jul. 21, 1994.

SNAP-25 also has two known isoforms (a and b) and an analogue called SNAP-23. As with VAMP there is a yeast analogue of SNAP-25 called SEC9.

Syntaxin has large number of isoforms, divided into groups 1–6 at the last count. Some of these isoforms have sub-groups e.g. 1a and 1b. In yeasts, there are a host of analogues of syntaxin, known a SED5, PEP12, SSO1 and SSO2.

The substrate for the assay is consequently conveniently selected from the group consisting of VAMP; VAMP analogues; VAMP isoforms; SNAP-25; SNAP-25 analogues; SNAP-25 isoforms; syntaxin; syntaxin analogues and syntaxin isoforms. References hereafter to VAMP, SNAP-25 and syntaxin are to be understood as references to all member of each family of proteins.

A further embodiment of the assay of the invention comprises:

(i) combining the test compound with a solid phase comprising a peptide selected from the group consisting of VAMP; VAMP analogs; VAMP isoforms; SNAP-25; SNAP-25 analogs; SNAP-25 isoforms; syntaxin; syntaxin analogs; and syntaxin isoforms, (ii) washing the test compound from the solid phase, (iii) combining the solid phase with an antibody adapted for binding selectively with peptide cleaved by toxin, and (iv) detecting conjugates of the antibody with cleaved peptide.

Preferably, the antibody is adapted to bind selectively to a peptide selected from SEQ ID NOS: 1–7.

Another embodiment of the assay comprises:

(i) adding a test solution to an assay plate comprising immobilized peptide, the peptide being selected from VAMP; VAMP analogs;

VAMP isoforms; SNAP-25; SNAP-25 analogs; SNAP-25 isoforms; syntaxin; syntaxin analogs; and syntaxin isoforms, (ii) incubating the assay plate, (iii) washing the plate with a buffer, (iv) adding to the plate an antibody solution, said solution comprising an antibody adapted selectively to bind to a peptide selected from (1) apeptide the C-terminal end of which is selected from SEQ ID NOS: 1, 3 and 5, and (2) a peptide the N-terminal end of which is selected from SEQ ID NOS: 2, 4 and 6, (v) incubating the assay plate, (vi) washing the plate with a buffer, and (vii) measuring the presence of antibody on the assay plate.

In steps (ii) and (v) a suitable incubation period is from twenty minutes to 3 hours, at 35–39° C.

In the method of the invention, the antibody can be linked to an enzyme and the antibody on the plate can be measured by adding a substrate and observing conversion into a detectable, e.g. colored, product. Other enzymes that may be used include, but are limited to, malate dehydrogenase, staphylococcal nuclease, delta-V-steroid isomerase, yeast alcohol dehydrogenase, alpha-glycerophosphate dehydrogenase, triose phosphate isomerase, alkaline phosphatase, asparaginase, glucose oxidase, beta-galactosidase, ribonuclease, urease, catalase, glucose-VI-phosphate dehydrogenase, glucoamylase and acetylcholine esterase.

Radioisotopes that may be linked to the enzyme of the invention include $^3$H, 125I, $^{131}$I, $^{32}$P, 35S, $^{14}$C, $^{51}$Cr, $^{36}$Cl, $^{57}$Co, $^{58}$Co, $^{59}$Fe and $^{75}$Se. Alternatively, the enzyme may be linked to a fluorescent compound such as fluorescein isothiocyanate, rhodamine, phycoerythrin, phycocyanin, allophycocyan, o-phthaldehyde and fluorescamine. Chemiluminescent compounds that can be linked to the enzyme include luminol, isoluminol, theromatic acridinium ester, imidazole, acridinium salt and oxalate ester. Bioluminescent compounds that may be linked to the enzyme include luciferin, luciferase, aequorin and green fluorescent protein.

It has already been noted that the assay of the invention detects active toxin in a compound or sample under investigation. Some toxins, notably botulinum toxins, exist also in an inactive conformation, and as such would not be identified by the assay. A further embodiment of the assay includes pre-treatment of the test compound or sample, to convert inactive toxin into active toxin. This is achieved for example by a protease, such as trypsin.

It is further preferred that the assay incorporates a substrate attached to a solid phase, for example covalently linked, such as via a terminal cysteine residue, to a solid phase of the assay.

The assay procedure of the invention thus typically represents a solid-phase microtitre based assay which can be applied to a number of specific toxins such as the botulinum neurotoxins and tetanus toxin. In contrast to spectrophotometric assays, the procedure of the invention can be easily automated and can be applied to very crude samples or particulate preparations of toxin endopeptidases. The procedure is also relatively inexpensive and easy to use.

For detection of antibodies bound to the cleaved substrate it is optional for the antibodies to be linked to a marker molecule or an enzyme. In an example, the marker is horse radish peroxidase which can be detected using conventional and well-known techniques.

In a particular embodiment of the invention, synthetic peptide substrates for the botulinum toxins (derived from sequences of intracellular proteins that are targets for the toxins) are prepared and used as the solid-phase endopeptidase substrate component in an assay system that follows the procedure:

Step 1—test solutions containing botulinum toxin are incubated with the solid—phase endopeptidase substrate. This results in the cleavage of the peptide at a specific point in the sequence which is dependant on the toxin type (this is illustrated in FIG. 1).

Step 2—incubation with antipeptide antibody reagent. This antibody reagent is specific to one of the newly cleaved N- or C-terminal ends of the solid-phase peptide and does not recognize the intact peptide. The antibody reagent is covalently conjugated to an enzyme marker, such as peroxidase or alkaline phosphatase. It is a further option to have present two separate antibodies that bind, respectively, one to the N-terminal ends and the other to the C-terminal ends of the newly cleaved peptides.

Step 3—incubation with substrate for the enzyme marker or further amplification by commercially available techniques.

It is seen that the assay of this latter embodiment has two main components.

The first component is an endopeptidase substrate component which contains or consists of a protein or peptide that is cleaved by the toxin endopeptidase to be assayed. This will typically be incorporated into the solid-phase component of the assay.

The endopeptidase substrate component may be, for example, the protein target of the endopeptidase (such as VAMP; VAMP analogs; VAMP isoforms;

SNAP-25; SNAP-25 analogs; SNAP-25 isoforms; syntaxin; syntaxin analogs; or syntaxin isoforms) or a fragment of these proteins that is cleaved by the toxin endopeptidase. The endopeptidase substrate component may alternatively be a fusion protein comprising the above linked to another protein.

The solid-phase may be an ELISA plate, bead, dip-stick or any other matrix that can be used for immobilizing the endopeptidase substrate component. The solid-phase component may also be a nitrocellulose membrane or the equivalent as used in the Western blotting technique. Alternatively, the solid phase may be conducted of diazocellulose, glass, polystyrene, polyvinylchloride, polypropylene, polyethylene, dextran, nylon, starch or affinity support gels such as Sepharose and agar.

The second component is the antibody component which is an antibody raised against a short polypeptide (typically 6–8 amino acid residues in length) representing the sequence of either the newly generated N- or the newly generated C-terminal peptide obtained after cleavage of the endopeptidase substrate component by the toxin endopeptidase. The antibody has the properties that it does not recognize the endopeptidase substrate component but instead recognizes only the cleaved peptide product.

The antibody may be linked to an enzyme, or a radioactive or fluorescent marker. Alternatively, the antibody may be the free protein and a second anti-antibody used in the assay procedure. In this embodiment, the first antibody may be derived from a first animal species and the second antibody may be specific for the antibody isotype of the first animal. The second antibody is prepared by immunizing a second animal species with the first antibody and isolating the second antibody. The antibody may further be polyclonal or monoclonal in make up, an antibody fragment, or an antibody or antibody-fragment fused or linked to another protein.

In a second aspect of the invention there is provided an antibody for use in the assay of the first aspect characterized by the following properties:

(a) the antibody binds to a peptide that is the product of cleavage of a substrate by a toxin endopeptidase, and (b) the antibody does not bind to the uncleaved substrate.

In an embodiment of the second aspect, the antibody does not bind to the substrate, which is linked covalently or otherwise to a carrier molecule. It is preferred that the substrate is a peptide, more preferably a nerve cell peptide, that is cleavable by a toxin according to the first aspect of the invention. The peptide is preferably selected from syntaxin, VAMP and SNAP-25.

It is further preferred that the peptide substrate is cleaved by the toxin endopeptidase at a limited number of locations, and preferably at two, or more preferably one, location so as to generate a limited number of cleavage products, and that the antibody binds selectively to one of these products.

In preferred embodiments of the invention the antibody recognizes one of the following peptide sequences:

| 1. | KAASSEF-n terminal | (SEQ ID NO:1) |
|---|---|---|
| 2. | LQAGASQ-c terminal | (SEQ ID NO:2) |
| 3. | RIDEANQ-c terminal | (SEQ ID NO:3) |
| 4. | GLMKTAR-n terminal | (SEQ ID NO:4) |
| 5. | QNRQIDR-c terminal | (SEQ ID NO:5) |
| 6. | SDAKEMI-n terminal. | (SEQ ID NO:6) |
| 7. | KAASTEF-n terminal. | (SEQ ID NO:7) |

Such peptides may be prepared by well known methods of solid phase synthesis.

The preferred antibodies do not recognize any one of the sequences 1–7 immediately above when that sequence is part of an intact, uncleaved peptide and tat sequence does not contain the free N- or C-terminal ends shown immediately above.

An antibody according to the second aspect of the invention and for use in a toxin assay is prepared, for example, by the procedure:

identifying a peptide that is cleaved by the toxin to generate a cleavage product, immunizing an animal, such as a rabbit, with the cleavage product, isolating antibodies to the cleavage product from the animal, and screening for antibodies that do not cross react with the peptide.

Another aspect of the invention provides a method of obtaining an antibody, the antibody being for use in a toxin assay, the method comprising identifying a macromolecule that is cleaved by a toxin into cleavage products, immunizing an animal against one of the cleavage products, isolating antibodies that bind to said one of the cleavage products and screening for antibodies that do not cross-react with the macromolecule. An embodiment of this method comprises:

(i) identifying a macromolecule that is cleaved by a toxin, thereby forming at least first and second cleavage products, (ii) immunizing an animal with one of the cleavage products, (iii) isolating from the animal antibodies that bind to the selected cleavage product, and (iv) screening for antibodies that do not bind to the macromolecule.

The macromolecule is preferably a peptide or a protein. It is particularly preferred that the peptide or protein is cleaved into two fragments.

The method enables production of antibodies that possess a surprising and advantageous property, in particular, for preforming assays for toxin. The property of interest is the binding affinity for the shortened cleavage product, uncontaminated by specific affinity of any significance to the intact, uncleaved macromolecule.

In another embodiment, the method comprises:

(i) identifying a peptide or protein that is cleaved by a toxin and subjecting said peptide or protein to cleavage by said toxin, thereby forming at least first and second cleavage products, (ii) immunizing an animal with an antigen selected from (1) a terminal fragment of the first cleavage product, (2) a synthetic fragment of the first cleavage product, (3) an analogue of (1) and (4) a carrier molecule linked to any of (1)–(3), (iii) isolating from the animal an antibody that binds to the first cleavage product.

Many carrier molecules are known in the art, and preferred carriers include keyhole limpet hemocyanin, bovine serum albumin and ovalbumin.

In a further aspect the invention provides a component of a toxin assay which is a peptide substrate immobilized to a solid phase of a toxin assay, the peptide substrate being a target for cleavage by a toxin endopeptidase. Preferably, the peptide is selected from the intact peptide and fragments of:

1. VAMP
2. SNAP-25
3. Syntaxin.

Particularly preferred target peptide sequences for use in the assay are selected from SEQ ID NOs. 8–11 illustrated below.

SEQ ID NO. 8 (VAMP isoform-1, aas 33–94):
QQTQAQVDEVVDIMRVNVDKVLER-DQKLSELDDRADALQAG ASQFESSAAKLKRKY-WWKNLK SEQ ID NO. 9 (VAMP isoform-1 aas 60–94):
LSELDDRADALQAGASQFESSAAK-LKRKYWWKNLK SEQ ID NO. 10 (SNAP-25 aas 137–206):
VTNDARENEMDENLEQVSGIIGNLRHM-ALDMGNEIDTQNRQID RIMEKADSNKTRIDE-ANQRATKMLGSG SEQ ID NO. 11 (VAMP isoform-2, aas 60–94):
LSELDDRADALQAGASQFETSAAK-LKRKYWWKNLK Further preferred peptides of the invention are peptides that include a sequence selected from SEQ ID NOS: 1–7.

The solid-phase peptides of the assay are stable and suitable for incorporation into test kits that provide for convenient and efficient toxin assays. Such test kits comprise a carrier means such as a box having in close confinement therein one or more container means such as vials, tubes, bottles, jars and the like, each of which contain one or more elements that are used in the assays of the invention. For example, a first contained means may contain antibodies which have specific binding affinity for a cleavage product of a peptide that has been cleaved by a toxin. A second container means may contain one or more substrates that are cleaved by the toxin. Additional container means may contain standard concentrations of toxin that can be used to prepare a standard curve for quantitation of toxin in a test sample.

It will be appreciated by those of ordinary skill that the assay of the invention can also be performed with a solid phase that comprises an antibody according to the second aspect of the invention immobilized thereto. With this arrangement, the assay is performed by combining the toxin substrate with the test compound that possibly contains toxin. This mixture is then combined with the immobilized solid-phase antibody and thereafter the presence of cleaved peptide bound to the solid-phase antibody is detected. In an embodiment of the invention, the cleaved peptide bound to antibody is detected using radiolabelled peptide or, alternatively, a further peptide specific antibody. Accordingly, a fourth aspect of the invention provides an immobilized solid-phase antibody for use in a toxin assay wherein the antibody has the binding properties according to the second aspect of the invention.

The assay procedures of the invention thus encompass various features:

(i) The production of an antibody to a polypeptide sequence (e.g. XXXXN) which is recognised only when amino acid N is free and not when the same sequence makes up a longer peptide (e.g. XXXXNXXXX). It is surprising that suitable antibodies can be raised that show non-reactivity to the longer peptide.

(ii) The use of the properties of such an antibody in a rapid, solid-phase assay for toxin endopeptidase. In the example of the botulinum or tetanus neurotoxin assay, the procedure exploits the zinc-endopeptidase activities of these toxins.

(iii) An assay that uses toxin target molecules, such as nerve cell peptides, as solid-phase assay components.

(iv) An assay that uses the antibodies described in (i) as solid-phase assay components.

A feature of the invention is that antibodies used to detect cleaved peptide do not bind to uncleaved peptide; for, clearly, such binding would generate false positives and compromise assay accuracy. A convenient means of determining that antibodies do not cross-react with intact peptide is to screen antibodies using two plates. The first contains intact peptide attached to a solid phase. The second contains cleaved peptide attached to a solid phase, a free end of the cleaved peptide being, for example, one of SEQ ID NOS: 1–7 or another sequence recognised by assay antibodies.

Antibodies under screening are added to both plates, allowed to incubate for a period and the plates are then washed and subsequently tested for the presence of bound antibody. Suitable antibodies, i.e. those with substantially no cross-reactivity, generate a large signal on the second plate, indicating the presence of bound antibody and a weak signal, preferably virtually no detectable signal, on the first plate.

If a number of potential assay antibodies are tested then it is straightforward to compare the ratio of signal (second plate result) to noise (first plate result) so that antibodies are selected with a high selectivity for cleaved peptide over intact peptide. In an embodiment of the invention, this ratio is at least 10:1, preferably at least 20:1 and more preferably at least 50:1. A particularly preferred ratio would be 100:1 or higher, reflecting an affinity for cleaved peptide at least 2 orders of magnitude greater than affinity for intact peptide.

The invention advantageously provides an assay that measures biological activity of the toxins, e.g. botulinum neurotoxin, and tetanus toxin, with a sensitivity comparable to that of a conventional ELISA system. The inventors have observed that the assay is capable of detecting less than 1 ng of toxin per ml in the case of botulinum A and B toxins. For many workers, accurate quantification of toxin would be highly desirable for use in risk assessment. Also, false negatives are unlikely as the assay is a direct measurement of toxin endopeptidase activity. The observations by the inventors are that assay noise levels in serum and other samples are significantly lower than those obtainable in conventional immunoassay systems. The inventors have to date had no false negatives or false positives with the assay for botulinum B toxin and the noise levels were lower in toxin samples containing serum than the noise levels that can be obtained with a conventional ELISA. Further, the peptide solid-phase assay component is stable with a very long shelf life.

The assay and assay components of the invention described are particularly sensitive for toxin and have been found by the inventors to have comparable and improved sensitivity to ELISAs for toxin. A further advantage of the invention is that it has potential to be more sensitive, as further specific antibodies are identified for use in the assay. Contrast this situation with that for ELISAs, which rely on antibody affinity for toxin. As this affinity is already optimal due to extensive work in isolating high affinity antibodies, few increases in ELISA sensitivity are expected.

There are many different sequences for the various members of the substrate protein families, and examples are given in the following published papers:

VAMP:

Archer, III, B. T., Ozcelik, T., Jahn, R., Francke, U. and Sudhof, T. C., "Structures and chromosomal localisations of two human gene encoding synaptobrevins 1 and 2," *J. Biol. Chem.* 265: 17267–17273 (1990).

SNAP-25:

Oyler, G. A., Higgins, G. A., Hart, RA., Battenberg, E., Billingsley, M., Bloom, F. E. and Wilson, M. C., "The identification of novel synaptosomal-associated protein SNAP-25, differentially expressed in neuronal subpopulations," *J. Cell Biology* 109: 3039–3052 (1989).

Schiavo, G., Santucci, A., DasGupta, B. R, Mehta, P. P., Jontes, J., Benfenati, F., Wilson, M. C., and Montecucco, C., "Botulinum neurotoxins serotypes A and E cleave SNAP-25 at distinct COOH-tenninal peptide bonds," *FEBS Lett.* 335: 99–103 (1993).

Syntaxin:

Bennett, M. K., Calakos, N., and Scheller, R. H., "Syntaxin: a synaptic protein implicated in docking of synaptic vesicles at presynaptic active zones," *Science* 257: 255–259 (1992).

Having now generally described this invention, the same will be better understood by reference to specific examples, which are included herein for purposes of illustration, and are not intended to be limiting unless otherwise specified.

EXAMPLE 1

An Assay for Botulinum Type B Neurotoxin (BoNT/B)

For the botulinum type B assay a peptide representing the sequence of VAMP isoform-1, residues 60–94 (SEQ ID NO:9, plus an C-terminal cysteine residue) was used:

LSELDDRADALQAGASQFESSAAK-LKRKYWWKNLKC

Microtitre assay plates were prepared as follows: The above peptide was diluted to a final concentration of 10 $\mu gml^{-1}$ in 0.05 M sodium phosphate buffer, pH 6.5 containing 1 mM EDTA and added (100 $\mu l$/well) to a Sulphydryl Binding Plate (Costar). After incubation for 1 hour at room temperature the peptide solution was removed and the plates washed 3 times with phosphate buffered saline (PBS), pH 7.4 (no detergent is used at this stage in the washing). Any remaining binding sites on the plates were then blocked by the addition (100 $\mu l$/well) of a PBS buffer containing 0.1% Tween 20 and 5% Foetal bovine serum. The plates were then incubated for one hour at 37° C. with continuous shaking after which the blocking solution was removed.

Assay of *Clostridium botulinum* type B neurotoxin: Toxin solutions were diluted in an assay buffer (e.g. 0.05M Hepes buffer, pH 7.4 containing 10 $\mu M$ $ZnCl_2$ and 1% foetal bovine serum) containing 10 mM dithiothreitol (or an equivalent reagent to provide reducing conditions for the endopeptidase activity of the toxins) and added (100 $\mu l$/well) to peptide coated microtitre plates. The plate is then incubated for one hour at 37° C. with continuous shaking. After this period in which BoNT/B cleaves the peptide as depicted in FIG. 1, the plates were washed 3 times with PBS containing 0.1% Tween 20.

Antibody specific to the newly cleaved peptide is then added. In this example of the assay, the antibody is specific to the following cleaved sequence of VAMP (SEQ ID NO: 1 plus C-terminal cysteine):

CKAASSEF-$NH_2$

The antibody (diluted in PBS buffer containing 0.1% Tween 20 and 5% foetal bovine serum) is added (100 $\mu l$/well) and incubated for one hour at 37° C. with continuous shaking. The plates were then washed 3 times with PBS containing 0.1% Tween 20.

If the antibody is conjugated to peroxidase, appropriate peroxidase substrates are added at this stage to develop the colour and provide the results of the assay.

An alternative is that the antibody is in its free form, in which case the S addition of a commercially available second antibody is required. If, for example, the anti-peptide antibody is raised in guinea-pigs, then this second antibody is an anti-guinea-pig peroxidase conjugate. The second antibody conjugate (diluted in PBS buffer containing 0.1% Tween 20 and 5% foetal bovine serum) is added (100 $\mu l$/well) and incubated for one hour at 37° C. with continuous shaking. After washing off the second antibody (×3 with PBS containing 0.1% Tween 20), appropriate peroxidase substrates may be added at this stage to develop the colour and provide the results of the assay.

FIG. 2 illustrates the results of a typical assay for BoNT/B using the two antibody detection system described above. The data illustrate the use of two different VAMP peptides as the solid-phase peptide in the assay. The sequences of these peptides near the cleavage site for BoNT/B represent the two isoforms of human VAMP.

VAMP-1 (60–94) LSELDDRADALQAGASQFESSAAK-LKRKYWWKNLKC (SEQ ID NO:9, plus C-terminal cysteine)

VAMP-2 (60–94) LSELDDRADALQAGASQFETSAAK-LKRKYWW LKC (SEQ ID NO:11, plus C-terminal cysteine)

The data show that, at an arbitrary cut-off point of 0.3 absorbency units above background, the sensitivity for the detection of BoNT/B in these assay was approximately 1 ng/ml using the VAMP-1 peptides as the solid-phase and approximately 5 ng/ml using the VAMP-2 peptides as the solid-phase.

FIG. 3 illustrates the specificity of the assay system for BoNT/B. Zero absorbency was recorded for (1) BoNT/F, (2) Tetanus toxin and (3) BoNT/B plus EDTA. These data show that an assay designed to detect BoNT/B did not give false-positive results in the presence of the closely related botulinum type F and tetanus toxins. The data also show that no signal was obtained in assays performed with BoNT/B in the presence of EDTA (which is a metal ion chelating agent). The latter result illustrates that the assay is dependent on the zinc-metalloprotease activity of BoNT/B.

FIG. 4 illustrates the assay kinetics of solid-phase peptide cleavage by BoNT/B using both the single antibody (i.e. antipeptide antibody directly conjugated to peroxidase) and dual antibody (i.e. in which the free antipeptide antibody is used in conjunction with a anti-species peroxidase conjugate) detection systems. The concentration of BoNT/B was fixed at 100 ng/ml and the assay signal measured at various times. The data show that the dual antibody assay system provides the more rapid and sensitive means with which to measure solid-phase peptide cleavage by BoNT/B.

EXAMPLE 2

Amplification and Enhancement of Assays for the Botulinum Neurotoxins

The are a number of ways in which the assays for the botulinum toxins such as that described in Example 1 may be further enhanced to provide greater sensitivity:

(a) Further amplification of the assay signal using commercially available amplification systems such as the ELAST™ (Dupont) system.

(b) Limited trypsin treatment of the neurotoxin prior to assay. All of the botulinum neurotoxins are produced, in the bacterium, as single polypeptide chains which are then subsequently activated by specific bacterial proteases to give the active, di-chain form of the toxin In some instances, notably in the case of botulinum neurotoxin types B and E, the toxins are not fully activated and can contain up to 100% inactive neurotoxin. These inactive, single chain, forms of the toxin express the endopeptidase activity of the toxin either weakly or not at all. Limited trypsin treatment of the botulinum neurotoxins converts the single chain toxin form to the di-chain, active toxin form. Thus, in botulinum neurotoxin types which contain a portion of single chain toxin, trypsin treatment results in both an increase in the endopeptidase activity and specific toxicity of the neurotoxin.

FIG. 5 illustrates the increase in sensitivity of an assay for BoNT/B when an amplification system such as the ELAST system is applied to a typical assay as described in Example 1. The data show that, at an arbitrary cutoff point of 0.3 absorbency units above background, the sensitivity for the detection of BoNT/B in the non-amplified assay was approximately 1 ng/ml while that in the amplified assay system was almost 10-fold higher giving a sensitivity close to 0.1 ng/ml.

The results show that the assay of the invention can be readily used in conjunction with commercially available amplification systems to provide improved sensitivity.

FIG. 6 illustrates the effect of limited trypsin treatment of BoNT/B on the sensitivity of the neurotoxin assay. BoNT/B samples (1 mg/ml) were treated with trypsin (final concentration of 2.5 µg/ml) for 30 min at 37° C. and the reaction stopped using a 5–10 molar excess of trypsin inhibitor. FIG. 6 shows that, for both the amplified and non-amplified forms of the assay, the effect of the trypsin treatment is to increase the sensitivity of the assay system for BoNT/B.

An alternative strategy for the assay for BoNT/B is performed using a different combination of solid-phase peptide substrate and specific antibody to cleaved sequences. In this aspect of the assay the solid-phase VAMP peptide is attached by an N-terminal cysteine residue (SEQ ID NO:9, plus N-terminal cysteine):

C L S E L D D R A D A L Q A G A S Q F E S S A A K-
    LKRKYWWKNLK

The specific antibody to the cleaved sequence in this embodiment of the invention is raised against the following cleaved sequence of VAMP:

LQAGASQ-COOH (SEQ ID NO:2)

EXAMPLE 3

An Assay for Tetanus Toxin

Tetanus toxin cleaves the protein VAMP at an identical site to that of BoNT/B. The specificities of the endopeptidase activities of the two toxins however differ in the minimum peptide substrate size required for cleavage. While BoNT/B requires peptide substrates of 30–35 residues in length for optimal cleavage, the requirement for tetanus toxin is peptide substrates of >50 residues in length.

Tetanus toxin cleavage assays are therefore carried out in an identical manner to those for BoNT/B with the exception that the solid-phase peptide is a peptide of human VAMP-1 isoform-1, residues 33–94 (SEQ ID NO:8). Example of the invention described for BoNT/B are equally applicable to tetanus toxin.

EXAMPLE 4

An Assay For Botulinum Type A Toxin (BoNT/A)

For the botulinum type A neurotoxin assay, microtitre plates are coated (10 µg/ml) with the following peptide representing a sequence taken from protein SNAP-25 (aas 137–206).

V T N D A R E N E M D E N L E Q V S G I I G N L R H M-
    ALDMGNEIDTQNRQID RIMEKADSNKTRIDE-
    ANQRATKMLGSG (SEQ ID NO:10)

Toxin test solutions buffered with 0.05M HEPES pH 7.2 containing 10 µM $ZnCl_2$ and 10 mM 2-mercaptoethanol are then added and the plate incubated at 37° C. for 1 h.

After washing the plates are then incubated with antipeptide antibody conjugated to horse radish peroxidase. The antibody is specific to either of the following cleaved sequences of SNAP-25:

| | |
|---|---|
| RIDEANQ-COOH | (SEQ ID NO:3) |
| GLMKTAR-$NH_2$ | (SEQ ID NO:4) |

After incubation the excess peptide is removed by washing and then the peroxidase substrates added to develop the colour.

Figure 7:
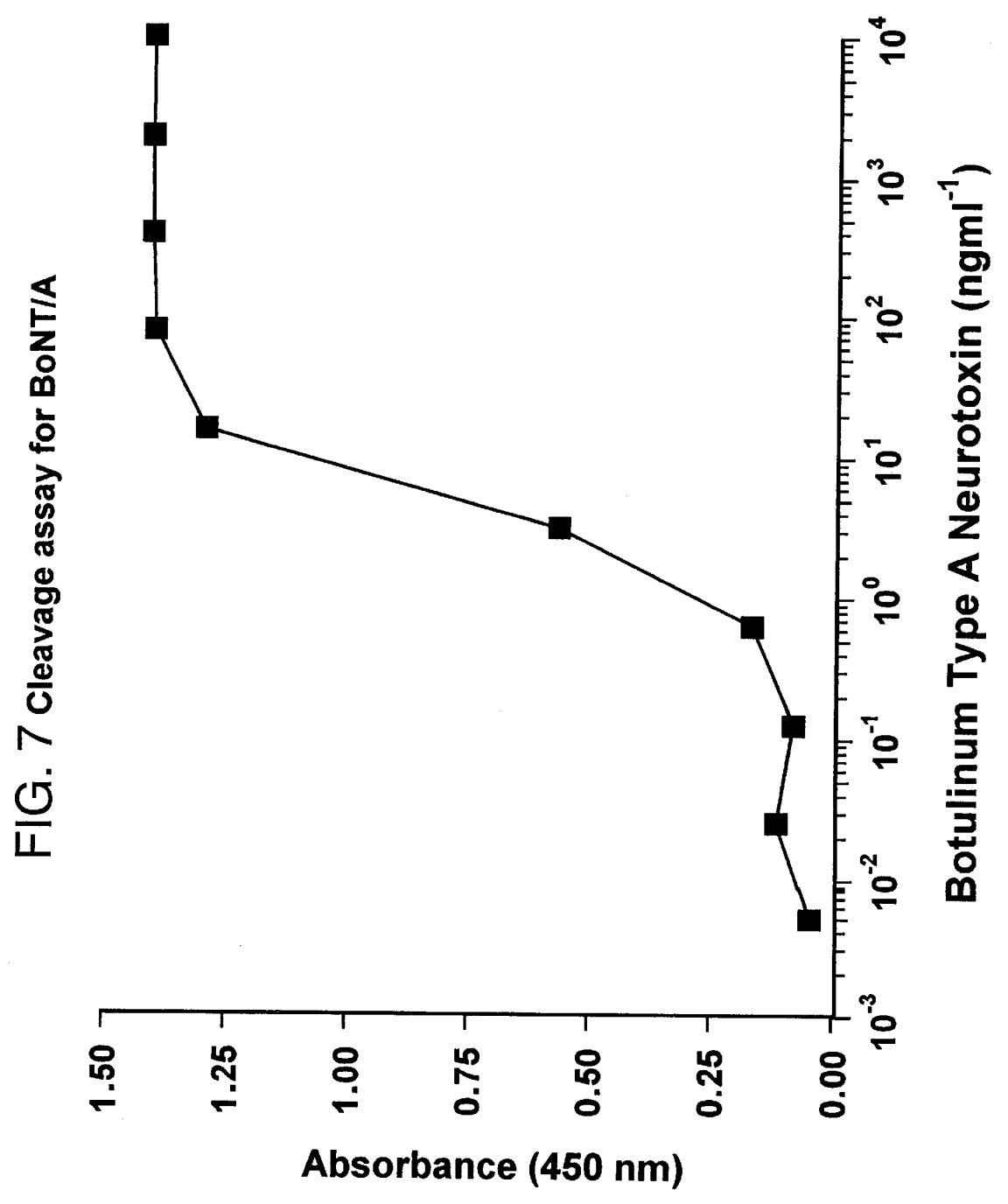

FIG. 7 shows the results of a typical assay for BoNT/A. In this assays system the solid-phase peptide was SNAP-25 (137–206) as depicted above, used in conjunction with antisera specific to the cleaved sequence of SNAP-25:

| | |
|---|---|
| RIDEANQ-COOH | (SEQ ID NO:3) |

Assay protocol was as described for BoNT/B in the Example 1. The assay detected BoNT/A at a concentration of approximately 1 ng/ml (using an arbitrary absorbency cut-off point of 0.3 units above background).

The amplification systems described in Example 1 may also be applied to assays for BoNT/A.

EXAMPLE 5

An Assay of Botulinum Type E Toxin

For the botulinum type E neurotoxin assay, microtitre plates are coated (10 µg/ml) with the following peptide representing a sequence taken from protein SNAP-25 (aas 137–206).

V T N D A R E N E M D E N L E Q V S G I I G N L R H M-ALDMGNEIDTQNRQID RIMEKADSMKTRIDE-ANQRATKMLGSG (SEQ ID NO:10)

Toxin test solutions buffered with 0.05M HEPES pH 7.2 containing 10 µM $ZnCl_2$ and 10 mM 2-mercaptoethanol are then added and the plate incubated at 37° C. for 1 h.

After washing the plates are then incubated with anti-peptide antibody conjugated to horse radish peroxidase. The antibody is specific to either of the following cleaved sequences of SNAP-25:

| QNRQIDR-COOH | (SEQ ID NO:5) |
| SDAKEMI-$NH_2$ | (SEQ ID NO:6) |

After incubation the excess peptide is removed by washing and then the peroxidase substrates added to develop the colour.

EXAMPLE 6

Preparation and Use of Microtitre Plates and Other Assay Solid Phases

Microtitre plate or dip-sticks are prepared by a number of different methods:

(a) Microtitre plates are coated (100 µl/well) with the "endopeptidase peptide substrate" at a concentration of 10 or 20 µg/ml in phosphate buffered saline pH 7.4 (or water) and incubated overnight at 4° C.

(b) The "endopeptidase peptide substrate" is produced with a cysteine residue at one end. The end of the peptide to which the cysteine residue is added is determined by the specificity of the antibody to be used in the assay. The peptide cleavage product (formed during the course of the assay) which is recognised by the specific antibody must also contain the cysteine residue at its distal end. The "endopeptidase peptide substrate" is diluted to a final concentration of 10 $\mu gml^{-1}$ in 0.05 M sodium phosphate buffer, pH 6.5 containing 1 mM EDTA and added (100 µl/well) to a Sulphydryl Binding Plate (Costar). After incubation for 1 hour at room temperature the peptide solution is removed and the plates washed 3 times with phosphate buffered saline, pH 7.4 (no detergent is used at this stage in the washing).

(c) A cysteine containing derivative of the "endopeptidase peptide substrate" (as above) is linked to a carrier protein (e.g. maleimide-activated BSA) which is commercially available (Pierce Warriner, U.K.) which is then bound to microtitre plates are described in (a) above.

(d) The "endopeptidase peptide substrate" is bound onto another solid-phase such as nitrocellulose membranes and procedures used similar to those defined in standard Western blotting techniques. The cleavage assay can be performed in several ways:

(i) The peptide substrate is cleaved on the nitrocellulose membrane.

(ii) The peptide is cleaved by botulinum toxin in solution and then the products bound to the nitrocellulose membrane.

(iii) The botulinum/tetanus toxin target proteins may be cleaved intracellularly (or in vivo) by the toxins, the cell extracts separated by SDS gel electrophoresis and then the cleaved peptide products transferred to nitrocellulose by Western blotting.

The plates are then washed with phosphate buffered saline (PBS) containing 0.1% Tween 20 and then blocked (to prevent further binding of proteins to the polystyrene) with a solution of 5% foetal calf serum in PBS (or 1% BSA in PBS or other blocking cocktails such as powdered milk in PBS).

Plates in this condition are suitable to be stored frozen for many months (or even years).

To perform the assay, test solutions of toxin are buffered with 0.25M Hepes pH 7.4 buffer containing 10 µM $ZnCl_2$ and 20 mM 2-dithiothreitol (toxin solution: buffer ratio of 4:1) and then added to microtitre plates and incubated for 1 hr at 37° C. The toxin test solution is then washed with PBS/tween and then an antibody-peroxidase conjugate added. (The antibody is specific to one exposed end of the cleavage product and is added at a pre-determined dilution depending on the batch). After incubation for 1 hr at 37° C. the antibody-peroxidase conjugate is washed off the plate with PBS/tween and then peroxidase substrates added to develop the colour.

EXAMPLE 7

Method of Specific Antibody Production

The peptides to which antibodies are to be raised are synthesised with a cysteine residue at the opposite end of interest. In Example 1, the two peptides synthesised are as follows:

| CKAASSEF-$NH_2$ | (SEQ ID NO:1, plus cysteine) |
| CLQAGASQ-COOH | (SEQ ID NO:2, plus cysteine) |

The peptide is then linked to a carrier protein (e.g. Keyhole Limpet Haemocyanin or Bovine Serum Albumin) via the cysteine residue. This is achieved by mixing the peptide with the maleimide-activated carrier protein (commercially available from Pierce Warriner, U.K.) as detailed by the suppliers.

The conjugated peptide is then injected in the presence of an adjuvant (e.g. Freund's adjuvant) into animals (e.g. guinea-pigs or rabbits). One immunisation schedule is to give animals 50 µg of the peptide-protein at times 0, 4 weeks and 8 weeks; animals are then bled after 10 weeks.

Antibody in serum is purified by any one of the published methods for purifying IgG from sera. Anti-peptide specific antibody is optionally further purified by affinity chromatography using the immunising peptide immobilised onto chromatography medium (kit and method commercially available from Pierce Warriner, U.K.).

Antibodies with the desired binding characteristics are assessed as describe in Example 6. The assay should not give a colour in the absence of toxin and should give a strong colour in the presence of 1 µg/ml of the desired toxin.

EXAMPLE 8

Quantification of the Assay

The assay is made quantitative by incorporating a toxin standard. The colour produced by various concentrations of the toxin is measured by a microtitre plate reader and a standard curve produced from which the toxin concentration in unknown samples may be assessed.

Thus the invention provides a novel and efficient toxin assay and provides novel reagents for use in the assay. The assay is inexpensive compared to existing assays, for example those using a mouse lethality test, and is suitable for industrial application.

EXAMPLE 8

Method of Antibody Production

STAGE 1. Peptides (e.g. those shown in example 7) were coupled, by the free cysteine, to Keyhole Limpet Haemocyanin (KLH) as described by the following protocol:
Coupling of peptide to Keyhole Limpet Haemocyanin (KLH) using m-Maleimidobenzoic acid N-hydroxysuccinimide ester (MBS).
1: Dissolve 4 mg of KLH in 1 ml of 10 mM sodium phosphate pH 7.2.
2: Dissolve 0.7 mg of MBS in 100 µl of dimethylformamide (DMF) and add dropwise to the KLH solution while stirring continuously. Stir the mixture for a further 30 min at room temperature.
3: Equilibrate a PD-10 gel filtration column with 50 mM sodium phosphate buffer pH 6.0. Run the KLH-MBS solution down the column and collect 10 ml fractions. Measure the absorbance of each fraction at 280 nm. The first peak eluted from the column is the required KLH-MBS. Pool these fractions.
4: Dissolve 5 mg of peptide in 1 ml of PBS. (If the peptide will not dissolve try other buffers e.g. 0.1M sodium borate pH 9, or 1M sodium acetate pH 4.) Remove 200 µl of this solution and carry out an Ellmans assay (see below).
5: Add the peptide to the KLH-MBS and adjust the pH to 7–7.5. Stir the solution at room temperature for 4 hours. Remove 200 µl and perform an Ellmans assay. The sample should give a pale yellow colouration at the end of this Ellman assay compared to a deep yellow colour before conjugation.
6: Dialyse the sample overnight against PBS at 4° C.
7: Estimate the concentration of protein in the conjugate using the Pierce BCA assay following the manufacturers recommended procedure.
Ellmans assay for free thiol.
8: Dissolve 4 mg of 5,5-dithiobis-2-nitrobenzoic acid (DTNB, Ellmans reagent) in 1 ml of 0.1M sodium phosphate buffer pH 8.
9: Set up a series of dilutions of cysteine.
10: Add 200 µl of the sample or cysteine standard to 200 µl of Ellman reagent and 1 ml of buffer. Allow to stand for 15 min and then read the absorbance at 412 nm. The amount of free thiol can then be determined from the cysteine standard curve.
STAGE 2. The KLH-peptide conjugate was then used to immunise animals by the following protocol:

| Day 1 | 50 µg in Freunds complete adjuvant |
|---|---|
| Day 15 | 50 µg in Freunds incomplete adjuvant |
| Day 29 | 50 µg in Freunds incomplete adjuvant |
| Day 43 | 50 µg in phosphate buffer saline |
| Day 54 | Test bleed |
| Day 55 | Bleed and recover serum |

This protocol is suitable for use with small animals including rabbits, guinea-pigs and rats. For use with larger animals such as goats or horses the doses should be increased to 1 mg or KLH-peptide.
Stage 3
The antibody is then purified from sera by affinity chromatography using columns of the immunising peptide immobilized onto Sulfolink (Pierce) according to the manufacturer's instructions.

All anti-peptide antibodies used to date are polyclonal in origin although it is just as feasible to perform the assay with monoclonal antibodies raised against the appropriate peptide.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those skilled in the art to which this invention pertains. All publications, patents and patent applications cited herein are incorporated by reference to the same extent as if each individual publication, patent or patent application was specifically and individually indicated to be incorporated by reference.

What is claimed is:

1. An antibody wherein said antibody does not bind to a protein selected from the group consisting of VAMP; a VAMP analog; a VAMP isoform; SNAP-25; a SNAP-25 analog; a SNAP-25 isoform; syntaxin; a syntaxin analog; and a syntaxin isoform; or a fragment thereof; but does bind to a peptide, wherein said peptide is formed by cleavage of said protein by a toxin, and wherein said peptide is selected from the group consisting of SEQ ID NOS: 1–6 and 7.

2. The antibody of claim 1, wherein said antibody binds to an antigen of formula:

P-Q-X wherein X is a peptide selected from the group consisting of SEQ ID NOS: 1–6 and 7 and is covalently linked at one end to P, wherein P is a carrier protein and Q is an amino acid or an amino acid sequence adapted to attach peptide X to carrier protein P.

3. An antibody, wherein said antibody does not bind to a protein but does bind to a peptide, wherein said protein is a substrate for botulinum toxin and is cleaved by botulinum toxin to form said peptide, and wherein said peptide is selected from the group consisting of SEQ ID NOS: 1–6 and 7.

4. The antibody of claim 3, wherein said protein is selected from the group consisting of VAMP, SNAP-25, syntaxin and analogs and isoforms thereof.

5. An antibody, wherein the binding affinity of said antibody is lower for a protein than for a peptide, and wherein said protein is a substrate for a toxin and is cleaved by said toxin to form said peptide, and wherein said peptide is selected form the group consisting of a SEQ ID NOS: 1–6 and 7.

6. The antibody of claim 5, wherein said toxin is tetanus toxin.

7. The antibody of claim 5, wherein said antibody essentially does not bind to said protein.

8. A method of obtaining an antibody, said method comprising identifying a macromolecule that is cleaved by a toxin into cleavage products, immunizing an animal against one of the cleavage products, isolating antibodies that bind to said one of the cleavage products and recovering antibody that does not cross-react with the macromolecule, wherein said one of the cleavage products is a peptide selected from the group consisting of SEQ ID NOS: 1–6 and 7.

9. The method of claim 8, wherein said macromolecule is selected from the group consisting of VAMP; a VAMP analog; a VAMP isoform; SNAP-25; a SNAP-25 analog; a SNAP-25 isoform; syntaxin; a syntaxin analog; a syntaxin isoform; and fragments thereof.

10. The method of claim 8, comprising:

(a) immunizing said animal with an antigen consisting of a peptide selected from the group consisting of SEQ ID NOS: 1–6 and 7, linked to a carrier molecule; and (b) isolating from said animal an antibody that binds to said antigen.

11. The method of claim 10, wherein said carrier molecule is selected from the group consisting of Keyhole Limpet Hemocyanin, Bovine Serum Albumin and Ovalbumin.

12. The method of claim 8, wherein said toxin is botulinum toxin.

13. The method of claim 8, wherein said toxin is tetanus toxin.

* * * * *

UNITED STATES PATENT AND TRADEMARK OFFICE
CERTIFICATE OF CORRECTION

PATENT NO. : 6,043,042

DATED : March 28, 2000

INVENTORS : Shone et al.

It is certified that an error appears in the above-identified patent and that said Letters Patent is hereby corrected as shown below.

On the title page, [73] Assignee name from "Microbiobiological Research Authority" to --Microbiological Research Authority--.

Signed and Sealed this

Sixth Day of March, 2001

Attest:

NICHOLAS P. GODICI

Attesting Officer   Acting Director of the United States Patent and Trademark Office

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 1:

Phe Glu Ser Ser Ala Ala Lys
1               5

(2) INFORMATION FOR SEQ ID NO: 2:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO: 2:

Leu Gln Ala Gly Ala Ser Gln
1               5

(2) INFORMATION FOR SEQ ID NO: 3:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO: 3:

Arg Ile Asp Glu Ala Asn Gln
1               5

(2) INFORMATION FOR SEQ ID NO: 4:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO: 4:

Arg Ala Thr Lys Met Leu Gly
1               5

(2) INFORMATION FOR SEQ ID NO: 5:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO: 5:

Gln Asn Arg Gln Ile Asp Arg
1               5

(2) INFORMATION FOR SEQ ID NO: 6:

(i) SEQUENCE CHARACTERISTICS:
             (A) LENGTH: 7 amino acids
             (B) TYPE: amino acid
             (C) STRANDEDNESS: single
             (D) TOPOLOGY: linear (ii) MOLECULE TYPE: peptide (xi) SEQUENCE DESCRIPTION: SEQ ID NO: 6:

Ile Met Glu Lys Ala Asp Ser
1               5

(2) INFORMATION FOR SEQ ID NO: 7:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 7:

Phe Glu Thr Ser Ala Ala Lys
1               5

(2) INFORMATION FOR SEQ ID NO: 8:

(i) SEQUENCE CHARACTERISTICS:
            (A) LENGTH: 62 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 8:

Gln Gln Thr Gln Ala Gln Val Asp Glu Val Val Asp Ile Met Arg Val
1               5                   10                  15

Asn Val Asp Lys Val Leu Glu Arg Asp Gln Lys Leu Ser Glu Leu Asp
                20                  25                  30

Asp Arg Ala Asp Ala Leu Gln Ala Gly Ala Ser Gln Phe Glu Ser Ser
            35                  40                  45

Ala Ala Lys Leu Lys Arg Lys Tyr Trp Trp Lys Asn Leu Lys
        50                  55                  60

(2) INFORMATION FOR SEQ ID NO: 9:

(i) SEQUENCE CHARACTERISTICS:
            (A) LENGTH: 35 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 9:

Leu Ser Glu Leu Asp Asp Arg Ala Asp Ala Leu Gln Ala Gly Ala Ser
1               5                   10                  15

Gln Phe Glu Ser Ser Ala Ala Lys Leu Lys Arg Lys Tyr Trp Trp Lys
                20                  25                  30

Asn Leu Lys
        35

(2) INFORMATION FOR SEQ ID NO: 10:

(i) SEQUENCE CHARACTERISTICS:
            (A) LENGTH: 70 amino acids
            (B) TYPE: amino acid
            (C) STRANDEDNESS: single
            (D) TOPOLOGY: linear -continued

```
    (ii) MOLECULE TYPE: peptide (xi) SEQUENCE DESCRIPTION: SEQ ID NO: 10:

Val Thr Asn Asp Ala Arg Glu Asn Glu Met Asp Glu Asn Leu Glu Gln
1               5                   10                  15

Val Ser Gly Ile Ile Gly Asn Leu Arg His Met Ala Leu Asp Met Gly
            20                  25                  30

Asn Glu Ile Asp Thr Gln Asn Arg Gln Ile Asp Arg Ile Met Glu Lys
        35                  40                  45

Ala Asp Ser Asn Lys Thr Arg Ile Asp Glu Ala Asn Gln Arg Ala Thr
    50                  55                  60

Lys Met Leu Gly Ser Gly
65                  70

(2) INFORMATION FOR SEQ ID NO: 11:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

Leu Ser Glu Leu Asp Asp Arg Ala Asp Ala Leu Gln Ala Gly Ala Ser
1               5                   10                  15

Gln Phe Glu Thr Ser Ala Ala Lys Leu Lys Arg Lys Tyr Trp Trp Lys
            20                  25                  30

Asn Leu Lys
        35
```